United States Patent [19]
Lantzsch et al.

[11] Patent Number: 5,840,983
[45] Date of Patent: Nov. 24, 1998

[54] PROCESS FOR PREPARING 2-TRIFLUOROMETHOXY-ANILINE

[75] Inventors: Reinhard Lantzsch, Wuppertal; Albrecht Marhold, Leverkusen, both of Germany

[73] Assignee: Bayer Aktiengesellschaft, Leverkusen, Germany

[21] Appl. No.: 896,353

[22] Filed: Jul. 18, 1997

[30] Foreign Application Priority Data

Jul. 26, 1996 [DE] Germany .................. 196 30 228.5

[51] Int. Cl.⁶ .................................................. C07C 211/02
[52] U.S. Cl. .................. 564/423; 564/417; 564/442; 564/443
[58] Field of Search .................. 564/417, 423, 564/442, 443

[56] References Cited

U.S. PATENT DOCUMENTS 4,059,627 11/1977 Kritzler et al. .
4,387,246 6/1983 Disdier et al. .

FOREIGN PATENT DOCUMENTS

| 0 054 464 A1 | 6/1982 | European Pat. Off. . |
| 0 143 769 A1 | 6/1985 | European Pat. Off. . |
| 0 546 391 A2 | 6/1993 | European Pat. Off. . |
| 2 024 249 | 12/1971 | Germany . |
| 25 49 900 A1 | 5/1977 | Germany . |

OTHER PUBLICATIONS

Sheppard, J.Org.Chem., vol 29, No. 1 (1964) "α–Fluorinated Ethers. I. Aryl Fluoroalkyl Ethers" pp. 1–11.

Primary Examiner—Brian M. Burn
Attorney, Agent, or Firm—Sprung Kramer Schaefer & Briscoe

[57] ABSTRACT

2-Trifluoromethoxy-aniline, which can be used as an intermediate for example for preparing pharmaceuticals and agrochemicals, is obtained in very good yields and high purity by nitrating in a first step 1,2-dichlorotrifluoromethoxy-benzene at temperatures between −20° C. and +80° C. and catalytically hydrogenating the resulting nitration products (exclusively 1,2-dichloro-5-nitro-4-trifluoromethoxy-benzene and 1,2-dichloro-3-nitro-4-trifluoromethoxy-benzene) in a 2nd step, it being possible to isolate the aniline intermediates corresponding to the two nitrobenzene derivatives; the nitrobenzene and aniline derivatives mentioned, being novel compounds, are also part of the subject matter of the invention.

9 Claims, No Drawings

PROCESS FOR PREPARING 2-TRIFLUOROMETHOXY-ANILINE

PROCESS FOR PREPARING 2-TRIFLUOROMETHOXY-ANILINE

The invention relates to a novel process and novel intermediates for preparing 2-trifluoromethoxy-aniline, known as a starting material for active compounds in medicine and agriculture.

2-Trifluoromethoxy-aniline is known to be obtainable by reacting 1-chloro-2-trifluoromethoxy-benzene with ammonia in the presence of a catalyst, such as, for example, copper(I) chloride, if appropriate in the presence of water, at temperatures between 200° C. and 280° C. (cf. EP 546391).

However, this reaction is technically complicated. The reaction is carried out under high pressure and at high temperatures, so that the required autoclave materials have to meet stringent requirements. Additionally, yields and qualities of the specific products obtained are not always entirely satisfactory.

It has now been found that 2-trifluoromethoxy-aniline of the formula (I)

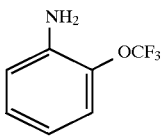

(I)

is obtained in very good yields and in high purity when in a first step 1,2-dichloro-4-trifluoromethoxy-benzene of the formula (II)

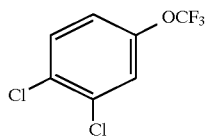

(II)

is reacted with a nitrating agent, if appropriate in the presence of a reaction auxiliary and/or diluent, at temperatures between −20° C. and +80° C.

and the resulting nitration products of the general formula (III)

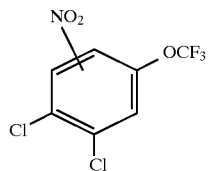

(III)

are reacted in a second step with hydrogen in the presence of a catalyst, in the presence of a diluent and, if appropriate, in the presence of a reaction auxiliary at temperatures between 0° C. and 200° C., it being possible to isolate the dichloro-trifluoromethoxy-aniline intermediates of the general formula (IV),

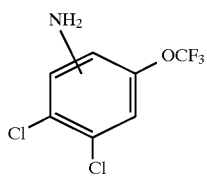

(IV)

if desired.

The general formula (I) represents the formulae (IIIA) and (IIIB)

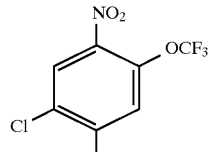

(IIIA)

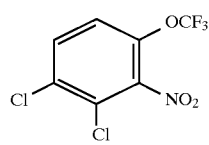

(IIIB)

The general formula (IV) represents the formulae (IVA) and (IVB)

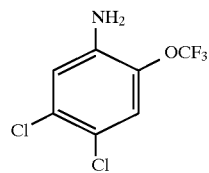

(IVA)

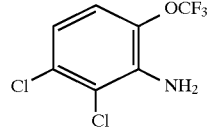

(IVB)

The compounds of the general formula (III)—i.e. the compounds of the formulae (IIIA) and (IIIB)—and the compounds of the general formula (IV)—i.e. the compounds of the formulae (IVA) and (IVB)—have hitherto not been disclosed in the literature; being novel substances, they also form part of the subject matter of the present application.

It has to be considered very surprising that the nitration of 1,2-dichloro-4-trifluoromethoxy-benzene of the formula (II) proceeds with high selectivity ortho to the trifluoromethoxy grouping and that virtually no 1,2-dichloro-6-nitro-4-trifluoromethoxy-benzene is formed, bearing in mind that in the nitration of 1-chloro-4-trifluoromethoxy-benzene almost identical amounts of 1-chloro-2-nitro-4trifluoromethoxy-benzene and 1-chloro-3-nitro-4-trifluoromethoxy-benzene are formed (cf. J. Org. Chem. 29 (1964), 1–11).

Both steps of the process according to the invention can be carried out in a simple manner employing standard equipment widely used in industry. It therefore represents a useful advance in the art.

The compound 1,2-dichloro-4-trifluoromethoxy-benzene of the formula (II) to be used as starting material in the process according to the invention is known or can be prepared in a known manner (cf. EP 546391; Preparation Examples).

The first step of the process according to the invention is carried out using a nitrating agent. Suitable nitrating agents are the customary agents used for nitrating aromatic organic compounds. These include in particular nitric acid, which can be employed in various aqueous dilutions—for example as conc. nitric acid (about 65% strength) or as fuming nitric acid (about 98% strength).

The first step of the process according to the invention is carried out, if appropriate, in the presence of a reaction auxiliary. Acids, such as, for example, sulfuric acid, are preferred reaction auxiliaries.

The first step of the process according to the invention is carried out, if appropriate, in the presence of a diluent. Suitable diluents are in particular relatively inert organic solvents, such as, for example, methylene chloride or chloroform However, it is also possible to use the reaction auxiliary acids already mentioned as diluents, too.

The reaction temperatures may be varied over a relatively wide range in the first step of the process according to the invention. Generally, the first step is carried out at temperatures between −20° C. and +80° C., preferably between −10° C. and +60° C., in particular between 0° C. and +40° C.

The first step of the process according to the invention is generally carried out at atmospheric pressure. However, it is also possible to carry out the first step of the process according to the invention at elevated or reduced pressure—in general between 0.1 bar and 10 bar.

To carry out the first step of the process according to the invention, generally 1 to 3 mol, preferably 1.1 to 2.5 mol, of nitrating agent are employed per mole of the starting material of the formula (II).

In a preferred embodiment of the first step of the process according to the invention, the starting material of the formula (II) is, if appropriate, initially charged together with a reaction auxiliary and/or a diluent and the nitrating agent is then slowly metered in. The reaction mixture is then stirred at the temperature required until the reaction has ended and then worked up in a conventional manner.

After the reaction has ended, the reaction mixture is, for example, mixed with ice water, extracted with a virtually water-immiscible organic solvent, such as, for example, methylene chloride, and the aqueous phase is reextracted several times. The combined organic phases are dried in a conventional manner and filtered. The solvent is carefully distilled off under reduced pressure from the filtrate, whereupon the nitration product of the formula (III)—i.e. the products of the formulae (IIIA) and (IIIB)—remains in the residue.

Generally, the intermediate of the formula (III) can be used for the reaction of the second step of the process according to the invention without any further purification; however, it is also possible to isolate the components of the formulae (IIIA) and (IIIB) by conventional methods, for example by distillation under strongly reduced pressure.

The second step of the process according to the invention is carried out in the presence of a catalyst. Preferred catalysts are the metal catalysts conventionally used in catalytic hydrogenations—if appropriate on suitable carrier materials. These are in particular (Raney) cobalt, (Raney) nickel, palladium and platinum (the latter, if appropriate, on a carrier material, such as, for example, activated carbon, clay, diatomaceous earth or alumina).

If the intermediates of the general formula (IV) are to be isolated, preference is given to using (Raney) nickel as catalyst in the presence of an organic compound inhibiting dehalogenation, such as, for example, thiodiglycol.

The second step of the process according to the invention is carried out in the presence of a diluent. Preferred diluents are water and organic solvents, in particular alcohols, such as methanol, ethanol, n- or i-propanol, n-, i-, s- or t-butanol; ethers, such as methyl t-butyl ether, methyl t-pentyl ether, ethylene glycol dimethyl ether or tetrahydrofuran; ether alcohols, such as ethylene glycol monomethyl ether or ethylene glycol monoethyl ether, furthermore hydrocarbons, such as hexane, cyclohexane, methylcyclohexane, toluene or xylenes, and also mixtures of the solvents mentioned.

Very particularly preferred diluents for the second step of the process according to the invention are alcohols, in particular methanol and ethanol.

The second step of the process according to the invention is carried out, if appropriate, in the presence of an acid acceptor as reaction auxiliary. Suitable acid acceptors are generally the customary inorganic or organic bases. These include preferably alkali metal or alkaline earth metal acetates, amides, carbonates, bicarbonates, hydrides, hydroxides or alkoxides, such as, for example, sodium acetate, potassium acetate or calcium acetate, lithium amide, sodium amide, potassium amide or calcium amide, sodium carbonate, potassium carbonate or calcium carbonate, sodium bicarbonate, potassium bicarbonate or calcium bicarbonate, lithium hydride, sodium hydride, potassium hydride or calcium hydride, lithium hydroxide, sodium hydroxide, potassium hydroxide or calcium hydroxide, sodium methoxide or potassium methoxide, sodium ethoxide or potassium ethoxide, sodium n- or i-propoxide or potassium n- or i-propoxide, sodium n-, i-, s- or t-butoxide or potassium n-, i-, s- or t-butoxide; and also basic organic nitrogen compounds, such as, for example, trimethylamine, triethylamine, tripropylamine, tributylamine, trioctylamine, tridodecylamine, ethyl-diisopropylamine, N,N-dimethyl-cyclohexylamine, dicyclohexylamine, ethyl-dicyclohexylamine, N,N-dimethyl-aniline, N,N-dimethyl-benzylamine, pyridine, 2-methyl-, 3-methyl-, 4-methyl-, 2,4-dimethyl-, 2,6-dimethyl-, 3,4-dimethyl- and 3,5-dimethyl-pyridine, 5-ethyl-2-methyl-pyridine, 4-dimethylamino-pyridine, N-methyl-piperidine, 1,4-diazabicyclo[2.2.2]-octane (DABCO), 1,5-diazabicyclo[4.3.0]-non-5-ene (DBN), and 1,8-diazabicyclo[5.4.0]-undec-7-ene (DBU).

The reaction temperatures may be varied over a relatively wide range in the second step of the process according to the invention. Generally, the second step is carried out at temperatures between 0° C. and 200° C., preferably between 10° C. and 150° C., in particular between 20° C. and 100° C.

The second step of the process according to the invention is generally carried out at atmospheric pressure or at elevated pressure, preferably between 1 bar and 100 bar, in particular between 1 bar and 50 bar.

In a preferred embodiment of the second step of the process according to the invention, the mixture of the intermediates of the formulae (IIIA) and (IIIB) defined by the formula (III) is initially charged in a suitable diluent, a catalyst and, if appropriate, a reaction auxiliary are added, and the hydrogenation is carried out in a conventional manner—preferably at elevated pressure and at elevated temperature. When the hydrogenation has ended, the remaining hydrogen is, if appropriate, displaced with nitrogen and the mixture is filtered. The solvent is distilled off from the filtrate under reduced pressure. The crude product remaining in the residue can be purified and isolated in a conventional manner.

The crude product is, for example, extracted with a virtually water-immiscible solvent, such as, for example, toluene, and dilute aqueous sodium hydroxide solution, and the organic phase is separated off and worked up by distillation under reduced pressure.

The compound 2-trifluoromethoxy-aniline of the formula (I) to be prepared by the process according to the invention can be used as an intermediate for preparing active compounds used in medicine and agriculture (cf. DE 2233845, DE 2601780, DE 2801316, U.S. Pat. No. 4,960,902, EP 524041, WO 94/14782).

PREPARATION EXAMPLES

Example 1
(first step of the process according to the invention)

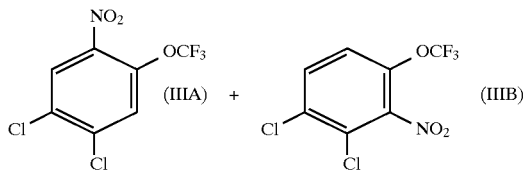

14.1 g (61 mmol) of 1,2-dichloro-4-trifluoromethoxy-benzene are initially charged in 183 ml of 96% strength sulfuric acid and 6.1 ml of 98% strength nitric acid are added dropwise, causing an exothermic reaction and increasing the inside temperature from initially about 20° C. to about 40° C. The reaction mixture is stirred for about 4 hours in this temperature range and then poured onto ice-water. The mixture is extracted three times with methylene chloride and the combined organic phases are washed with water, dried with sodium sulfate and filtered. The solvent is carefully distilled off from the filtrate using a water pump vacuum.

15.8 g of a yellow liquid containing 87.9% of 1,2-dichloro-5-nitro-4-trifluoromethoxy-benzene (IIIA) and 11.4% of 1,2-dichloro-3-nitro-4-trifluoromethoxy-benzene (IIIB) are obtained.

This corresponds to a total yield of 93.2% of theory.

Example 2
(second step of the process according to the invention)
(without isolating the intermediates of the formula (IV))

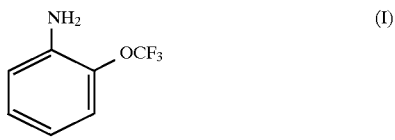

2.5 g (9 mmol) of the product mixture of Example 1 are dissolved in 30 ml of methanol, admixed with 0.3 g of palladium on activated carbon (5%) and hydrogenated for about 5 hours at about 30° C. and 10 bar hydrogen pressure. The catalyst is separated off by filtration and washed with a little methanol, and the filtrate is concentrated using a water pump vacuum. The residue is taken up in toluene and stirred with 5% strength aqueous sodium hydroxide solution. The organic phase is separated off and worked up by distillation under reduced pressure.

0.8 g (51% of theory) of 2-trifluoromethoxy-aniline of boiling point 60° C. (at 15 mbar, Kugelrohr) are obtained.

Example 3
(second step of the process according to the invention)
(without isolating the intermediates of the formula (IV))

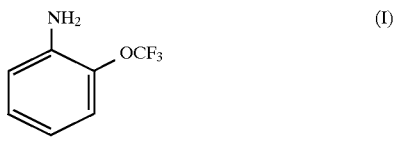

16 g (58 mmol) of the product mixture of Example 1 are dissolved in 300 ml of methanol, admixed with 6 g of palladium on activated carbon (5%) and with 22 g (119 mmol) of tributylamine and hydrogenated for about 5 hours at about 30° C. and about 10 bar hydrogen pressure. The catalyst is separated off by filtration and washed with a little methanol, and the filtrate is concentrated using a water pump vacuum. The residue is taken up in water and the mixture is made alkaline using 5% strength aqueous sodium hydroxide solution and extracted with toluene. The organic phase is separated off and worked up by distillation under reduced pressure.

29.7 g of a distillate consisting of 2-trifluoromethoxy-aniline and tributylamine, which are separated by fractional distillation, are obtained.

Yield: 8.1 g (78.6% of theory).

Intermediates of the formula (IV):

Example (IV -1)

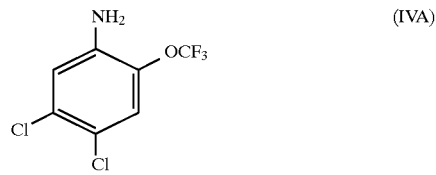

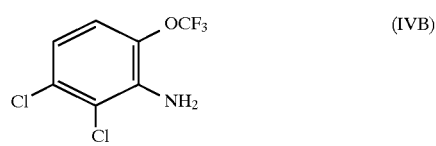

16 g (58 mmol) of the product mixture of Example 1 are dissolved in 400 ml of methanol and admixed with a drop of thiodiglycol [S(CH$_2$-CH$_2$OH)$_2$]. After the addition of 2 g of Raney nickel, the mixture is hydrogenated for about 5 hours at about 30° C. and about 5 bar hydrogen pressure. The catalyst is separated off by filtration and washed with a little methanol, and the filtrate is concentrated using a water pump vacuum The residue is worked up by distillation under reduced pressure.

11.4 g of 4,5-dichloro-2-trifluoromethoxy-aniline (IVA) with a boiling range of 86° C. to 94° C. (at 15 mbar) are obtained.

The isomeric 5,6-dichloro-2-trifluoromethoxy-aniline (IVB) can be isolated from the first cut of the distillation (up to 85° C., at 15 mbar).

Starting materials of the formula (II):

Example (II-1)

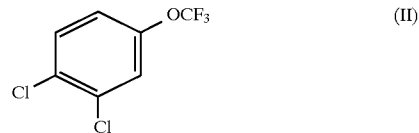

In a stainless VA-steel autoclave, 200 g (1.22 mol) of 3,4-dichloro-phenol and 800 ml of hydrogen fluoride are initially charged at 0° C. and 800 ml of carbon tetrachloride are added. After applying a pressure of 15 bar of nitrogen, the mixture is heated to 116° C. to 120° C. with vigorous stirring and the hydrogen chloride formed is released at about 28 bar. The formation of hydrogen chloride ceases after about 7 hours, whereupon excess hydrogen fluoride is distilled off together with trichlorofluoromethane and carbon tetrachloride. The subsequent distillation of the residue at from 60° C. to 86° C. (17 mbar) affords 213 g of a product mixture consisting of 19.2% of 1,2-dichloro-4-trifluoromethoxy-benzene and 80.1% of 1,2-dichloro-4-chlorodifluoromethoxy-benzene. This mixture is heated together with 100 ml of hydrogen fluoride and 1 ml of antimony pentachloride to about 125° C. for about 3 hours, and the hydrogen chloride formed is released at about 25 bar. The subsequent distillation affords 155 g (53% of theory) of 1,2-dichloro-4-trifluoromethoxy-benzene of boiling point 62° C. at 17 mbar.

I claim:

1. Process for preparing 2-trifluoromethoxy-aniline of the formula (I)

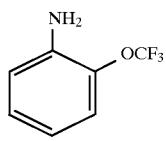 (I)

characterized in that in a first step 1,2-dichloro-4-trifluoromethoxy-benzene of the formula (II)

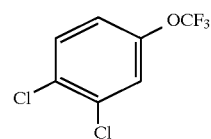 (II)

is reacted with a nitrating agent, if appropriate in the presence of a reaction auxiliary and/or a diluent, at temperatures between −20° C. and +80° C.
and the resulting nitration products of the general formulae (IIIA) and (IIIB)

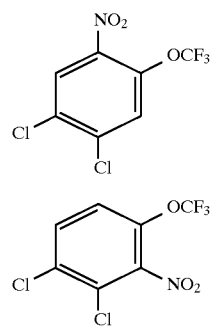

are reacted in a second step with hydrogen in the presence of a catalyst, in the presence of a diluent and, if appropriate, in the presence of a reaction auxiliary, at temperatures between 0° C. and 200° C.,
it being possible to isolate the intermediate dichloro-trifluoromethoxy-anilines of the general formulae (IVA) and (IVB)

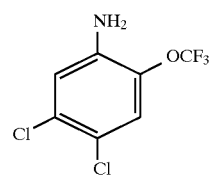 (IVA)

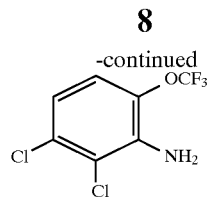 (IVB)

if so desired.

2. Process according to claim 1, characterized in that the first process step is carried out at temperatures between −10° C. and +60° C.

3. Process according to claim 2, characterized in that the first process step is carried out at temperatures between 0° C. and +40° C.

4. Process according to claim 1, characterized in that the second process step is carried out at temperatures between 10° C. and 150° C.

5. Process according to claim 4, characterized in that the second process step is carried out at temperatures between 20° C. and 100° C.

6. Process according to claim 1, characterized in that the second process step is carried out at a pressure in the range of from 1 bar to 100 bar.

7. Process according to claim 6, characterized in that the second process step is carried out at a pressure in the range of from 1 bar to 50 bar.

8. 1,2-Dichloro-5-nitro-4-trifluoromethoxy-benzene of the formula (IIIA) and 1,2-dichloro-3-nitro-4-trifluoromethoxy-benzene of the formula (IIIB)

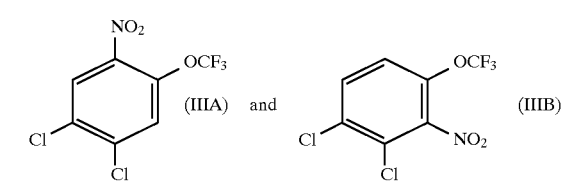

9. 4,5-Dichloro-2-trifluoromethoxy-aniline of the formula (IVA) and 5,6-dichloro-2-trifluoromethoxy-aniline of the formula (IVB)

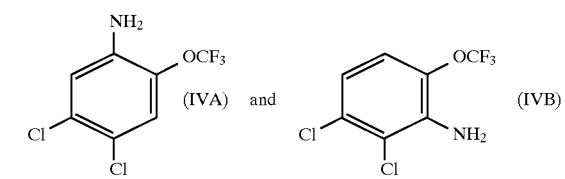

* * * * *

UNITED STATES PATENT AND TRADEMARK OFFICE
CERTIFICATE OF CORRECTION

PATENT NO : 5,840,983
DATED : November 24, 1998
INVENTOR(S): Reinnhard Lantzsch, et al.

It is certified that error appears in the above-identified patent and that said Letters Patent is hereby corrected as shown below:

Title Page, "Abstract", Lines 4-5  after "step" and before "-benzene" delete "1,2-dichlorotrifluoromethoxy" and substitute --1,2-dichloro-4-trifluoromethoxy--

Signed and Sealed this

Sixteenth Day of November, 1999

Attest:

Q. TODD DICKINSON

*Attesting Officer*   *Acting Commissioner of Patents and Trademarks*